United States Patent [19]

Patel et al.

[11] Patent Number: 4,788,064
[45] Date of Patent: Nov. 29, 1988

[54] TRANSDERMAL DELIVERY SYSTEM

[75] Inventors: Niranjan M. Patel, Dover; Mohan B. Kabadi, Marlboro; Susan C. Moniot, Chester, all of N.J.

[73] Assignee: Warner-Lambert Company, Morris Plains, N.J.

[21] Appl. No.: 79,965

[22] Filed: Jul. 31, 1987

[51] Int. Cl.[4] ............................................. A61F 13/00
[52] U.S. Cl. ..................................... 424/444; 424/448
[58] Field of Search .............................. 424/448, 449

[56] References Cited

U.S. PATENT DOCUMENTS

| | | | |
|---|---|---|---|
| 4,278,673 | 7/1981 | Hartley et al. | 514/243 |
| 4,631,227 | 12/1986 | Nakamura | 424/448 |
| 4,680,172 | 7/1987 | Leeson | 424/448 |
| 4,687,481 | 8/1987 | Nuwayer | 424/449 |
| 4,690,683 | 9/1987 | Chien et al. | 424/449 |

Primary Examiner—Thurman K. Page
Assistant Examiner—L. R. Home
Attorney, Agent, or Firm—Ronald A. Daignault

[57] ABSTRACT

The administration of a bronchodilator to a subject can be carried out using a new transdermal delivery system, a multilayer laminate where the drug is mixed in a gel which must pass through a barrier membrane prior to administration on the skin.

7 Claims, 2 Drawing Sheets

TRANSDERMAL DELIVERY SYSTEM

BACKGROUND

Procaterol has the chemical name 8-hydroxy-5]1-hydroxy-2-(1-methylethyl)amino]butyl]-2-(1H)-quinolone. It is known as a bronchodilator and has selective beta-adrenergic agonist activity. The compound and its preparation are described in U.S. Pat. No. 4,026,897, which is hereby incorporated by reference.

While the drug is highly efficacious, its use is subject to such problems as dose dumping and high drug usage requirements.

THE INVENTION

It has been discovered that procaterol and pharmaceutically acceptable salts thereof can be administered via the use of a transdermal system.

In a preferred embodiment, procaterol HCl is combined with linoleic acid, propylene glycol, triacetin, Wickenol R535, and Aerosil R200 to produce a gel composition which is used in combination with a barrier membrane as part of a multilaminated product to deliver the drug transmembranally, e.g., transdermally, to a subject.

ADVANTAGES

The delivery system of the invention has several advantages over other procaterol-based formulations. The gastrointestinal problems often associated with some drugs which are administered orally are eliminated.

The gradual release of the drug via membranal tissue, e.g., on the skin or in the nasal passage(s), minimizes the risk of dose dumping and other side effects.

In addition, the use of the instant system would result in a reduction in overall drug loading dose.

Furthermore, a patch or other transdermal device serves as a reminder to the patient to administer the proper dosage.

These and other advantages of the invention will become apparent upon consideration of the following description of the invention.

DESCRIPTION OF THE INVENTION

The invention deals with:

a device used to administer compositions through living cutaneous tissue, e.g., a patch. Such a device is preferably a multilayer laminate comprising (a) an impermeable backing whose perimeter contains an adhesive;

(b) a composition of a drug component admixed in a gel or saturated sponge layered on the inside of the backing;

(c) a barrier membrane covering the composition, and (d) a release liner covering the barrier membrane.

The barrier membrane used in such a device is generally a porous plastic material having a thickness of about 0.01 to about 0.08, preferably 0.02 to 0.04 mm.

Suitable plastic materials include those which are chemically inert to the components of the composition.

Thus, polyolefins, e.g., polypropylene, polyethylene, and polyesters, e.g., polyethylene terephthalate, or nylon are operable. Polypropylene is preferred. Blends of plastics are operable.

The impermeable backing to be used to support the composition and porous membrane layers should be about 2 mil to about 5 mil in thickness. It should be a strong, yet flexible material so that a bandage, foil, or other suitable supportive structure could be fashioned using it. Suitable materials include aluminum, metallized polyester, polyurethane, polyethylene, and the like.

The perimeter of the impermeable backing contains a silicone or acrylic medicinal grade adhesive laminate on the backing for sticking to cutaneous tissue.

The release liner which covers and holds in place both the drug gel (drug in the transmembranal composition) and the barrier membrane, is made of polyethylene or silicone coated film. The release liner is removed when placing the device or patch onto cutaneous tissue.

The composition or drug gel suitable for the transmembranal administration of procaterol contains:

(a) about 0.1 to about 5 weight percent procaterol or a pharmaceutically acceptable salt thereof, (b) about 5 to about 30 weight percent of an essential acid;

(c) about 15 to about 40 weight percent of a solvent for (a), and (d) about 25 to about 55 weight percent of a cosolvent for (a).

The basic components of the instant compositions are three: (1) a drug component, (2) a permeation enhancement component, and (3) a carrier component.

The phrase "procaterol and pharmaceutically acceptable salts thereof" is intended to include all forms of procaterol and/or its analogs which have medicinal utility. Thus, procaterol, procaterol HCl, procaterol lauryl sulfate, and the like are contemplated. Mixtures may be used.

While the use of a procaterol-based drug is essential to the invention, the use of other beneficial substances is also contemplated. Thus, sedatives, tranquilizers, antihistamines, cardiotonics, cognition activators, and the like may be included in the compositions of the invention.

Generally, the drug component will comprise about 0.1 to about 5.0, preferably 0.5 to about 1.0, and most preferably about 1.0 percent, of the total composition.

All percentages recited herein are weight percentages based on total composition weight unless otherwise indicated.

The permeation enhancement component is a combination of substances which function to assist in the migration of the drug component(s) through the membranes and into the bloodstream. Thus, any agent(s) which function to hasten the transmembranal passage or systemic release of the drug(s) can be used.

It is required that the permeation enhancement system contain at least one essential fatty acid. While linoleic acid is preferred, other essential fatty acids, such as oleic or linoleic, can be used. Mixtures are operable.

It is also required that the permeation enhancement component contain at least one solvent for the drug component. Useful solvents include, but are not limited to propylene glycol, triacetin, triethyl citrate, dimethylisosorbide, propoxylated cetyl alcohol (Wickenol 171), PEG-8, capric/caprylic triglyarides (Softigen 737) and the like. Mixtures of two or more are operable.

When two solvents are employed, it is preferred that both be present in amounts between about 15 and about 55 percent. A mixture of propylene glycol and triacetin as cosolvents is preferred.

In a propylene glycol/triacetin system, propylene glycol shall be present between about 15 to about 40 percent and preferably about 30 percent; while triacetin should be present at about 25 to about 55 percent, preferably about 40 to about 45 percent, most preferably at about 43.5 percent.

The carrier component contains one or more substantially inert ingredients which function to give the composition physical properties such that it can be effectively administered transmembranally. For example, the carrier component may be a sponge such that the composition will be effectively administered transmembranally and retained behind the barrier membrane. Suitable materials for such sponges include polyethylene, EVA, polyurethane, and the like.

Generally, the carrier(s) used will give the compositions either rheological or form properties such that they can be employed in storable multilayered devices.

Other carriers which give useful characteristics to the gel compositions of the invention are thixotropic agents. Colloidal silicas, such as Aerosil R200 (a commercial product of DeGussa) are preferred siliceous thixotropic agents. Other fillers include thixcin, cetyl alcohol, fatty acid triglycerides, and the like. Mixtures are operable.

An alternate and sometimes preferred carrier system may comprise about 0.01 to about one percent, preferably about 0.5 of an antiirritant such as Wickenol R535 and about one to about ten percent, preferably about five percent thixotropic agent. The composition is preferably used in a gel as one layer of a device to be affixed to the skin.

Other conventional adjuncts, e.g., colorants, perfumes, stabilizers, and the like can also be employed in suitable quantities in the compositions of the invention.

The following example illustrates one embodiment of the invention.

EXAMPLE

The gel described below was employed within a system consisting of a multilaminated impermeable backing of polyester heat sealed to the barrier membrane which is porous polypropylene of 0.02 to 0.04 $\mu$m thickness.

The drug-containing gel composition contained:

| Ingredients | Percent (%) |
| --- | --- |
| (1) Procaterol HCl | 1.00 |
| (2) Linoleic acid | 20.00 |
| (3) Propylene glycol | 30.00 |
| (4) Triacetin | 43.50 |
| (5) Wickenol R535 (wheat germ glycerides) | 0.50 |
| (6) Aerosil R200 (Colloidal Silicon Dioxide) | 5.00 |

In vitro permeation experiments carried out utilizing the transdermal gel system have demonstrated superior permeation profiles for procaterol across hairless mouse skin when compared to a PVC/VA matrix system. The permeation profile is set out in FIG. 1.

The other ingredients (layers) used in the patch were polyester backing and acrylic adhesive.

Figure 1:
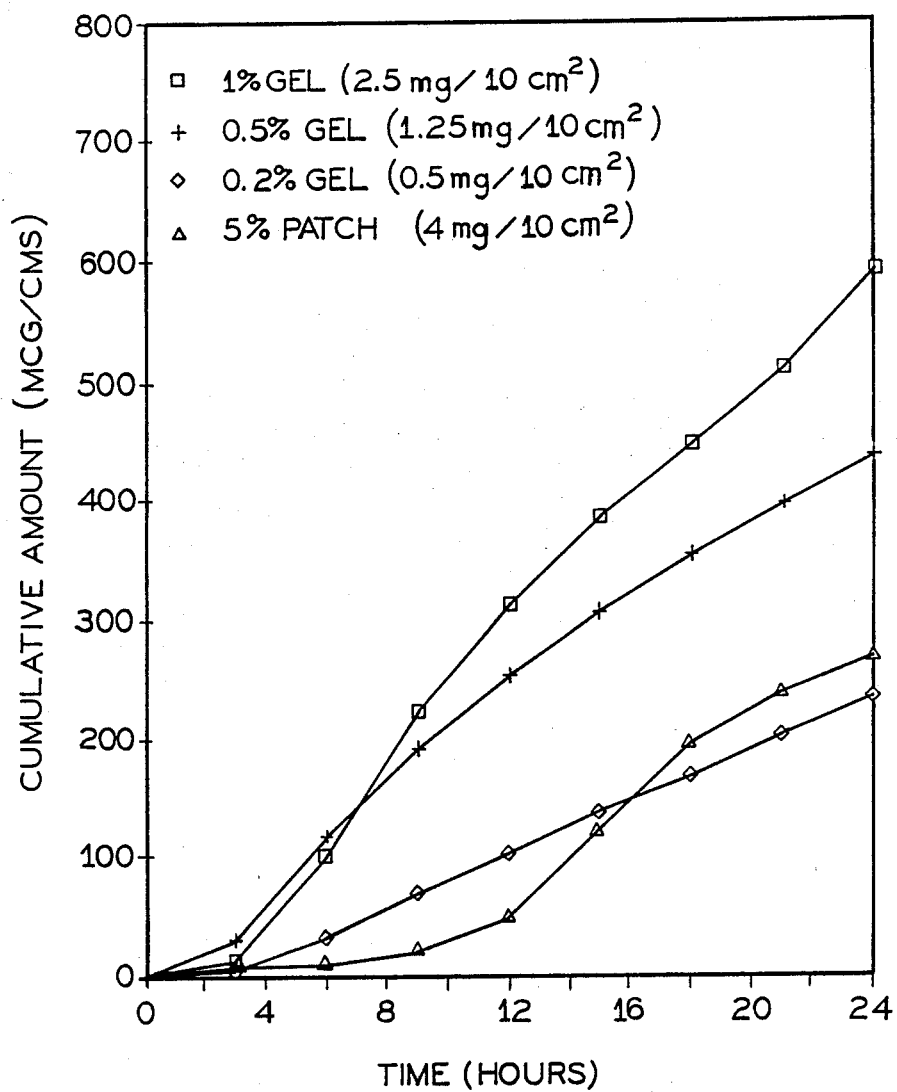
FIG. 1 shows a graph which plots the cumulative amount of drug which permeated hairless mouse skin against time. The graph is based on data generated in the example and shows in vitro permeation of procaterol HCl across hairless mouse skin from Hercon patch and 0.2 to 1% gel utilizing the flow thru cells.
Figure 2:
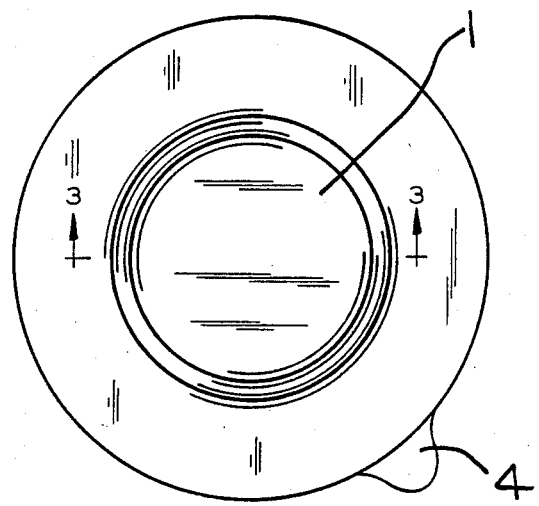
FIG. 2 is a cross-sectional and a topview of the multilayer laminate, the patch.
"1" is the impermeable backing;
"2" is the drug gel composition;
"3" is the barrier membrane;
"4" is the release liner, and
"5" is the adhesive on the perimeter of the impermeable backing.
Figure 3:
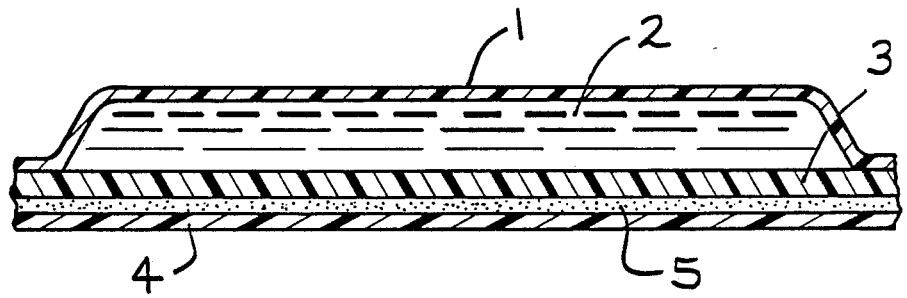

Reasonable variations, such as those which would occur to a skilled artisan, can be made herein without departing from the scope of the invention.

We claim:
1. A multi-layered device for the transmembranal delivery of procaterol comprising: an impermeable backing whose perimeter contains an adhesive; a composition saturated in a synthetic sponge layered on the inside of the backing wherein the composition comprises
    (a) about 0.1 to about five weight percent procaterol or pharmaceutically acceptable salt thereof;
    (b) about five to about 30 weight percent of an essential fatty acid;
    (c) about 15 to about 40 weight percent of a solvent for (a), and
    (d) about 25 to about 55 weight percent of a cosolvent for (a);
a porous barrier membrane covering the composition; and a release liner covering in turn the barrier membrane and adhered to the backing.

2. The device of claim 1 wherein the barrier membrane is a plastic material having a thickness of about 0.01 to about 0.08 mm.

3. The device of claim 2 wherein the barrier membrane has a thickness of 0.02 to 0.04 mm.

4. The composition of claim 1 wherein (a) comprises procaterol hydrochloride.

5. The composition of claim 1 which further contains: (e) about 0.01 to about one weight percent of an antiirritant, and (f) about one to about ten weight percent of a thixotropic agent.

6. The composition of claim 5 wherein (a) comprises procaterol hydrochloride.

7. The composition of claim 6 which contains: about 20 weight percent of (b), about 30 weight percent of (c), and about 40 to about 45 weight percent of (d).

* * * * *